(12) United States Patent
Bouloumie et al.

(10) Patent No.: US 6,284,277 B1
(45) Date of Patent: Sep. 4, 2001

(54) STABLE FREEZE-DRIED PHARMACEUTICAL FORMULATION

(75) Inventors: Colette Bouloumie; Thierry Breul, both of Montpellier; Laurence Colliere, Montbartier; Philippe Faure, Maurin, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/066,387

(22) PCT Filed: Oct. 30, 1996

(86) PCT No.: PCT/FR96/01706

§ 371 Date: Dec. 9, 1998

§ 102(e) Date: Dec. 9, 1998

(87) PCT Pub. No.: WO97/17064

PCT Pub. Date: May 15, 1997

(30) Foreign Application Priority Data

Nov. 3, 1995 (FR) .................................................. 95/13022

(51) Int. Cl.⁷ .................................................. A61K 9/14
(52) U.S. Cl. ............................................ 424/489; 424/450
(58) Field of Search ...................................... 424/489, 450

(56) References Cited

U.S. PATENT DOCUMENTS

| 4,537,883 | 8/1995 | Alexander et al. . |
|---|---|---|
| 5,558,880 | 9/1996 | Gole et al. . |
| 5,885,486 | * 3/1999 | Westesen et al. ............... 252/311 |

FOREIGN PATENT DOCUMENTS

| 394045 | 10/1990 | (EP) . |
|---|---|---|
| 682944 | 11/1995 | (EP) . |
| 2021581 | 12/1979 | (GB) . |
| WO 93/23017 | 11/1993 | (WO) . |

OTHER PUBLICATIONS

Chemical Abstract, 83:183393 (1975).
Derwent Abstract, 75–85480W (1975).
Derwent Abstract, 90–151822 (1990).
Patent Abstracts of Japan, vol. 14, No. 294 (C–732) (1990).
Derwent Abstracts of EP682944.

\* cited by examiner

*Primary Examiner*—Thurman K. Page
*Assistant Examiner*—R. Joynes
(74) *Attorney, Agent, or Firm*—Paul E. Dupont; Michael D. Alexander

(57) ABSTRACT

The subject of the invention is a freeze-dried formulation consisting of an amorphous phase and a crystalline phase, which is pharmaceutically acceptable, comprising at least one nonprotein active ingredient, characterized in that it contains mannitol and alanine in a ratio R of between 0.1 and 1, R representing the mass of mannitol to the mass of alanine.

13 Claims, 2 Drawing Sheets

STABLE FREEZE-DRIED PHARMACEUTICAL FORMULATION

Figure 1:
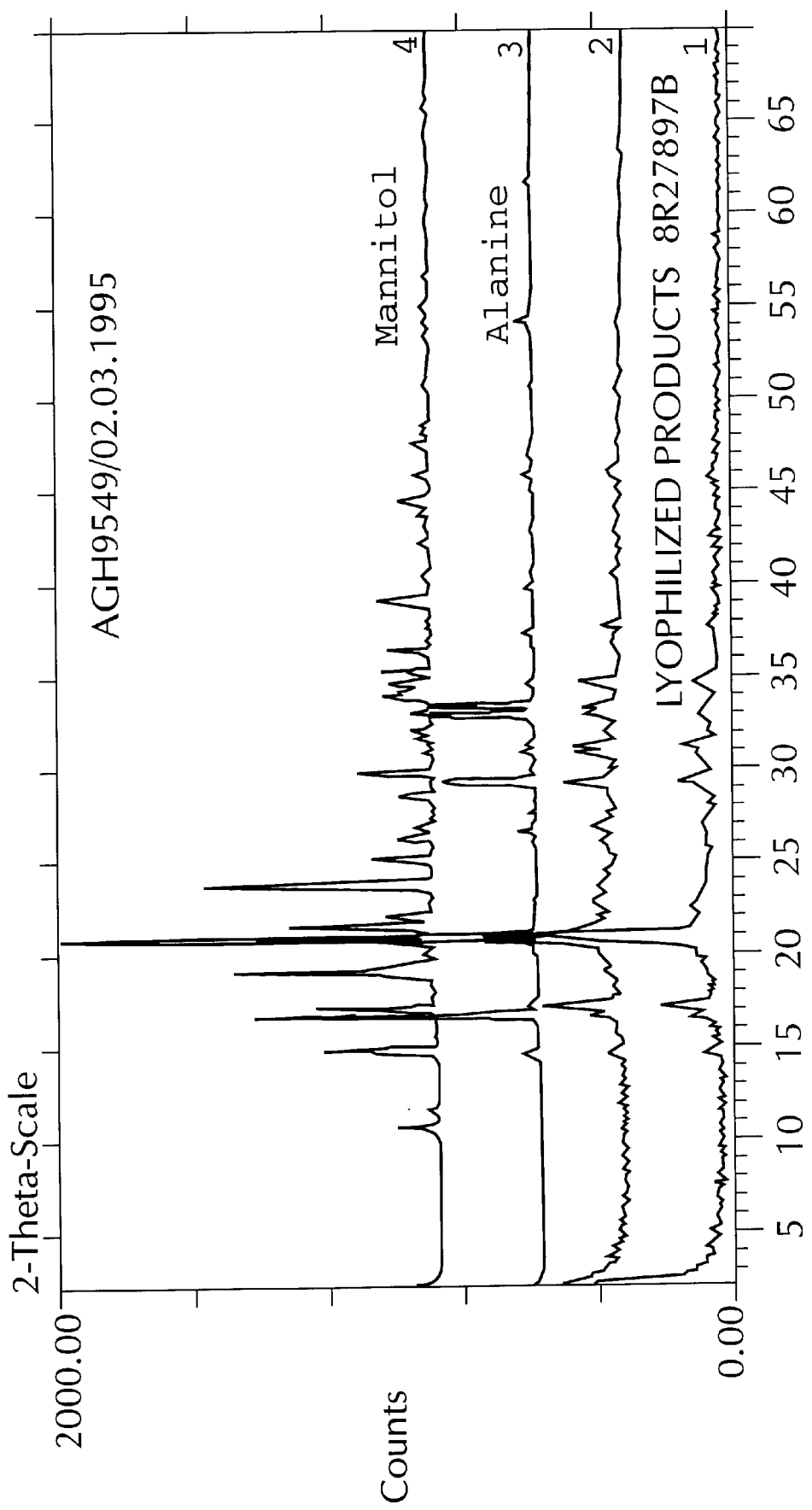

This application is a 371 of PCT/FR 96/01706 filed Oct. 30, 1996.

The present invention relates to a pharmaceutical formulation provided in the form of a freeze-dried product and containing at least one active ingredient of nonprotein nature. More particularly, the invention relates to such a formulation, stable at temperatures which may be as high as 25° C. to 40° C., which may be either reconstituted in liquid form by addition of a solvent for its administration via the parenteral or oral route, or directly administered via the oral route, to man or to animals.

The active ingredient contained in the formulation according to the invention may be alone or else combined with another active ingredient of protein or nonprotein nature.

It is known that freeze-drying may have a considerable effect on the degradation of the pharmaceutical active ingredients in a formulation, as well as a strong impact on their stability in freeze-dried form. The various variables which affect these parameters are mainly the pH, the quantity of salts present, the type and quantity of excipients in the formulation, the type of cryoprotection chosen, as well as the temperatures, pressure and time chosen for the freezing, sublimation and drying operations. These different variables influence the physical state of the freeze-dried product obtained, namely: vitreous amorphous, soft amorphous, crystalline or a combination of these states.

For the preservation of the freeze-dried products, amino acids, preferably glycine, and polyols, preferably mannitol, are often used; but the literature, which is highly abundant on the subject, gives no information on the solution to the general problem of obtaining a stable pharmaceutical formulation which takes into account the different parameters involved in the operations for formulating and freeze-drying a nonprotein active ingredient in combination with an amino acid and a polyol.

More particularly, the literature teaches that the presence of an amino acid, of a polyol, for example mannitol, of a crystalline phase or of an amorphous phase may have, besides certain advantages, disadvantages which lead, in the case of freeze-dried products containing particularly sensitive active ingredients, to relatively short shelf lives and/or storage temperatures for these freeze-dried products which are less than 8° C. It would, however, be particularly advantageous, especially for an ambulatory treatment, to be able to obtain a formulation which is stable at room temperature until it is reconstituted and to thereby avoid its storage in a refrigerator before or during treatment.

The role of the polyol and of amino acid has been studied separately in the case of the human growth hormone (hGH), but their synergistic effect is still poorly elucidated (Pikal M. J., Dellermann K. M., Roy M. L., Riggin M. N., The effects of formulation variables on the stability of freeze-dried Human Growth Hormone, Pharm. research., 1991, 8, No. 4, 427–436).

The advantages and disadvantages linked to the presence of amino acids, of mannitol, of a crystalline phase or of an amorphous phase are listed below.

Advantages linked to the presence of amino acids.

It has been demonstrated that the presence of glycine in a freeze-dried product induced crystallization of the molecules present in solution during the freezing stage of the freeze-drying (Korey D. J., Schwartz J. B., Effects of excipients on the cristallization of pharmaceutical compounds during lyophylization, J. Parenteral Sci. Tech., 1989, 43, 2, 80–83). This crystallization of the active ingredient makes it possible to enhance its stability.

Alanine, in crystallized form, has the advantage of preventing the collapse of the freeze-dried product during sublimation and drying and or allowing the production of a freeze-dried product with a greater specific surface area and therefore allows a more rapid drying (Pikal M. J., Freeze-drying of proteins, Biopharm., 26–30 October 1990).

Disadvantages linked to the presence of amino acids.

The addition of an amino acid to a sugar or to a polyol in a solution to be freeze-dried generally has the effect of decreasing the glass transition temperature of the sugar (te Booy M. P. W. M., de Ruiter R. A., de Meere A. L. J., Evaluation of the physical stability of freeze-dried sucrose containing formulations by differential scanning calorimetry, Pharm. Research., 1992, 9, 109–114). Now, a decrease in the glass transition temperature is generally synonymous with a lower stability of a freeze-dried product (Franks F., Freeze-drying; from empiricism to predictability, Cryo-letters, 1990, 11, 93–110).

Advantages linked to the presence of mannitol.

The presence of mannitol in the composition of a freeze-dried product is generally justified as freeze-drying ballast, that is to say that it makes it possible both to maintain the solid and rigid structure of the volume of the freeze-dried product corresponding to the volume of solution to be freeze-dried, but its presence also makes it possible to adjust the isotonicity of the reconstituted solution to be injected. When mannitol is the predominant excipient in the composition of a freeze-dried product, it is most often in crystalline form (Lyophilized formulations recombinant tumor necrosis factor, Hora M. S., Rana R. K., Smith F. W., Pharm. Res., 1992, 9 (1), 33–36).

Disadvantages linked to the presence of mannitol.

It has been reported that the degree of hydrolysis of methylprednisolone sodium succinate, in freeze-dried form, was greater in the presence of mannitol than in the presence of lactose, and that this level increased with the quantity of mannitol present in the freeze-dried product. This has been explained by the fact that the crystallization of mannitol during freeze-drying changes the distribution of water in the matrix of the freeze-dried product. The increase in the quantity of water present in the microenvironment of the active ingredient resulting therefrom enhances the hydrolysis of the active ingredient and reduces its stability (The effect of bulking agent on the solid state stability of freeze dried methylprednisolone sodium succinate, Herman B. D., Sinclair B. D., Milton N., Nail S. L., Pharma. Res., 1994, 11 (10), 1467–1473).

Advantages linked to the presence of a crystalline phase.

The presence of a crystallized solute in a frozen solution is a means of stabilizing the proteins during drying (Carpenter J. F. & Crowe J. H., Modes of stabilization of a protein by organic solutes during dessiccation, Cryobiology, 1988, 25, 459–470). Furthermore, the crystallization, during freezing, of the predominant excipients present in a solution to be freeze-dried makes the secondary sublimation and drying operations more effective by increasing the specific surface area for exchange between the atmosphere in the freeze-drying vessel and the solid to be sublimed. This increase in the specific surface area of the crystalline forms compared with the amorphous forms facilitates heat exchanges during freeze-drying. The consequence of this increased efficiency in the freeze-drying is the production of freeze-dried forms whose residual water content is lower, which means an increased stability of the freeze-dried product at higher temperatures (Korey D. J., Schwartz. J. B., Effects of excipients on the cristallization of pharmaceutical compounds during lyophylization, J. Parenteral Sci. Tech., 1989, 43, 2, 80–83).

Disadvantages linked to the presence of a crystalline phase.

In general, the crystallized substances have less rapid dissolution rates than the amorphous substances. Indeed, more energy is required to detach a molecule from an organized lattice of a crystalline arrangement than to detach it from a disorganized assembly of an amorphous state. Sometimes, the dissolution rate becomes insufficient to allow a sufficiently rapid absorption of these substances, which may lead to a decrease in their activity, especially in the case of molecules which are not very stable in solution. Likewise, the perfect regularity of crystals being an ideal case, the heterogeneity of the crystalline phase and the polymorphism which are obtained for the same substance and between associated substances induce different rates of dissolution for the same substance and between each of the substances, which may result in unreproducible therapeutic effects (Galénica 2, Biopharmacie 2nd edition, 1982, technique and documentation).

In addition, it has been demonstrated that the loss of activity of a freeze-dried protein was directly linked to the degree of crystallinity of the cryoprotective molecule (Izutsu K. L., Yoshioka S., Terao T., Decreased protein-stabilizing effects of cryoprotectants due to crystallization, Pharm. Research. 1993, 10, No. 8, 1232–1237; Izutsu K. I., Yoshioka S., Kojima S., Increased stabilizing effects of amphiphilic excipients on freeze drying of lactate dehydrogenase (LDH) by dispersion into sugar matrixes, Pharm. Res., 1995, 12 (6), 838–843). In the formulation of medicines containing proteins, the crystallization of the excipients should be avoided according to: (Hermansky M., Pesak M., Lyophilization of drugs, VI Amorphous and Cristalline forms Cesk. Farm., 1993, 42, (2), 95–98).

Advantages linked to the presence of an amorphous phase.

Based on the same line of thinking, the amorphous form dissolves more rapidly than the crystallized form and does not exhibit the disadvantages linked to the heterogeneity and to the polymorphism of the crystallized substances.

Moreover, the presence of additives in the amorphous state stabilizes the activity of certain enzymes proportionally to the concentration of the additive according to Izutsu K. L., Yoshioka S., Terao T., Decreased protein-stabilizing effects of cryoprotectants due to crystallization, Pharm. Research., 1993, 10, No. 8, 1232–1237.

The cryoprotective effect of the excipients is attributed to the amorphous state of the glycine in the freeze-dried product obtained (Pikal M. J., Dellermann K. M., Roy M. L. Riggin M. N., The effects of formulation variables on the stability of freeze-dried Human Growth Hormone, Pharm. Research., 1991, 8, No. 4, 427–436).

Disadvantages linked to the presence of an amorphous phase.

In the presence of a solid amorphous phase alone, the freeze-dried product collapses at temperatures greater than the glass transition temperature during freezing. Within a soft amorphous phase, the chemical degradation reactions have much more rapid kinetics than within a crystalline phase (Solid state stability and preformulation study of a new parenteral cephalosporin antibiotics (E1040), Ashizawa K., Uchikawa K., Hattori T., Ishibashi Y., Miyake Y., Sato T., Yakugaku Zasshi, 1990, 110 (3), 191–201).

Furthermore, the higher rate of dissolution of the amorphous substances is sometimes accompanied by a greater instability, the conversion of a form generally occurring from the amorphous state to the crystallized state (Galénica 2, Biopharmacie 2nd edition, 1982, technique et documentation).

In conclusion, the scientific literature on the subject of the effect of excipients on the stabilization of pharmaceutical active ingredients gives contradictory information on their properties and furthermore does not make it possible to obtain some information on the subject of the relationships between the structure of a freeze-dried product and its stability. Likewise, the role of the polyols and of the amino acids, alone or in combination, is not described according to a set of generalizable properties, but has been observed with contradictory results according to the active principles studied and the quantities of excipients used.

It has now been found that a synergistic effect exists between mannitol and alanine on the stabilization of freeze-dried pharmaceutical active ingredients. It has in particular been demonstrated that this synergistic effect exists only in a narrow range of relative concentrations of each of these two excipients.

The discovery of a surprising synergistic effect resulting from the coexistence of an amorphous phase and a crystalline phase which has the consequence of stabilizing the freeze-dried pharmaceutical active ingredient forms the basis of the present invention. The present invention therefore describes the production of this effect for specific mannitol/alanine ratios.

Thus, the present invention relates to a freeze-dried pharmaceutical formulation consisting of an amorphous phase and a crystalline phase, comprising an effective quantity of at least one nonprotein pharmaceutical active ingredient, mannitol and alanine, the latter two excipients being in a mass ratio R of between 0.1 and 1, R being the ratio of the mass of the mannitol to the mass of the alanine. The active ingredient included in the said formulation remains stable at temperatures which may range from 25° C. to 40° C. in freeze-dried form. Where appropriate, the dissolution of the freeze-dried product obtained is rapid and complete. The freeze-dried product does not have a collapsed appearance and its water content is compatible with maintaining the stability of the active ingredient.

It has been demonstrated that, for R of between 0.1 and 1:

the freeze-dried product consists of an amorphous phase and a crystalline phase, the amorphous phase predominantly consists of mannitol and active ingredient, the crystalline phase predominantly consists of alanine Although the invention is not limited to a specific theory which explains the stabilization obtained by combining one or more nonprotein active ingredients, mannitol and alanine in the indicated ratios, the following hypothesis can be made:

the amorphous phase, demonstrated by differential scanning calorimetry, cryoprotects the pharmaceutical active ingredient during freezing, the active ingredient itself being dispersed in this amorphous form, and the crystalline phase, demonstrated by X-ray diffractometry, fixes the structure of the freeze-dried product and avoids its collapse.

According to another of these features, the subject of the present invention is the production of stable freeze-dried products containing a pharmaceutical active ingredient cryoprotected by an amorphous solid phase consisting completely or partially of mannitol, this amorphous phase coexisting within the freeze-dried product obtained after sublimation and drying of the frozen solution, with a crystalline phase consisting essentially of alanine.

Thus, the subject of the present invention is also a process for the preparation of freeze-dried pharmaceutical formulations comprising at least one nonprotein active ingredient characterized in that a mixture of the said active ingredient, mannitol and alanine in which the mannitol and alanine are present in the ratio of between 0.1 and 1, R being the ratio of the mannitol mass to the alanine mass,is freeze-dried.

Other pharmaceutically acceptable excipients normally used in freeze-dried forms may be introduced into the formulation according to the present invention, such as for example buffers or acid-bases which make it possible to adjust the pH, surfactants, salts, preservatives, especially antibacterial preservatives, antioxidants or chelating agents, excluding excipients which, in the freeze-dried product containing the active ingredient, would prevent the coexistence of the crystalline phase consisting predominantly of mannitol and of the crystalline phase consisting predominantly of alanine, such as for example certain protein derivatives of animal or plant origin such as gelatines, dextrins or proteins extracted from wheat grain or soya bean, gums such as agar or xanthan, polysaccharides, alginates, carboxymethylcelluloses, pectins, synthetic polymers such as polyvinylpyrrolidone or complexes of a polysaccharide nature such as acacia gelatine. Among the buffers which may be introduced into the formulation according to the present invention, there may be mentioned in particular carbonate, borate, phosphate, citrate, tri(hydroxy-methyl)aminomethane, maleate and tartrate buffers, it being understood that the acids and bases composing said buffers may also be introduced alone. Among the surfactants which may be introduced into the formulation according to the present invention, there may be mentioned in particular polysorbates, poloxamers, tyloxapol, lecithins. Among the salts which may be introduced into the formulation according to the present invention, there may be mentioned in particular the sodium salts such as ededate (tetrasodium EDTA), chloride, docusate (sodium 1,4-bis(2-ethylhexyl)sulphosuccinate), bicarbonate, glutamate; potassium acetate; dipotassium carbonate and magnesium stearate.

Among the preservatives which may be introduced into the formulation according to the present invention, there may be mentioned in particular methyl and propyl para-hydroxybenzoate, benzethonium chloride, sodium mercurothiolate, phenylmercuric nitrate, benzyl alcohol, phenol and metacresol.

The coexistence of the amorphous mannitol phase and the crystalline alanine phase is independent of the presence and of the concentration of the buffer used to adjust the pH of the solution, but it depends on the ratio R defined above.

Examples of formulation of the solutions to be freeze-dried leading to the formulations of the invention are the following:

One or a combination of pharmaceutical active ingredients, a pharmaceutically acceptable buffer for adjusting the pH, mannitol and alanine with a mass ratio R=mass of mannitol/mass of alanine of between 0.1 and 1, water for injectable preparations, as well as, if necessary, antibacterial preservatives and excipients which allow solubilization of the active ingredient or ingredients. According to a preferred embodiment of the invention, the alanine/mannitol mixture is predominant.

The quantity of active ingredient present is limited by its solubility in water. The formulations of the invention indeed result from the freeze-drying of aqueous solutions in which the active ingredient is perfectly dissolved.

Likewise, any excipient is present in the formulation in a quantity below the quantity of the alanine/mannitol mixture.

The solutions to be freeze-dried are prepared in the following manner:

The desired quantities of buffer, alanine, mannitol, preservatives and active ingredient are added, at the appropriate dissolution temperature, to the quantity of water for injectable preparations or of solubilizing agent necessary for their solubilization until complete dissolution is obtained. The solutions obtained are filtered in a sterile medium and distributed into containers, preferably vials or capsules.

The freeze-drying of the solutions is carried out as follows:

The solution follows a cycle comprising freezing, then sublimation and drying adapted to the volume to be freeze-dried and to the container containing the solution.

Preferably, a freezing rate close to −2° C./min is chosen in an Usifroid (France) freeze-drier type SMH15, SMJ100 or SMH2000.

The sublimation and drying times, temperatures and pressures are adjusted according to the volumes of solution to be freeze-dried and the residual water content desired in the freeze-dried product.

A freeze-dried product is then obtained in which the alanine exists in crystallized form, and the mannitol in a completely or partially amorphous form. The freeze-dried product may be stored at 25° C. and even up to 40° C. without adversely affecting the chemical and biological stability of the active ingredient which it contains.

Full information on the techniques of preparation of injectable formulations by dissolution of the compositions of the invention is available to a person skilled in the art in Remington's Pharmaceutical Sciences, 1985, 17th Edition or in William N. A. & Polli G. P., The lyophilization of pharmaceuticals: a literature review, J. Parenteral Sci. Tech., 1984, 38, (2), 48–59 or in Franks F., Freeze-drying: from empiricism to predictability, Cryo-letters, 1990, 11, 93–110.

The active ingredient or the combined active ingredients, of the nonprotein type, formulated according to the present invention may be analgesics, anti-inflammatory agents, antispasmodic agents, anticancer agents or active ingredients which can be used in cardiology, angiology, gastroenterology, haematology and haemostasis, hepatology, infectiology, neurology-psychiatry, rhinology, rheumatology, toxicology, urology, or in the diagnostic field or as metabolism and nutrition regulators.

In the therapeutic families and the field of biological activity which are mentioned above by way of example, any product can constitute the active ingredient of the formulations of the present invention which represent a considerable technical advance in the pharmaceutical technique. Preferably, the active ingredients which are most adapted to the formulations of the present invention are those whose stability in aqueous solution is problematical. It is however conceivable to apply the present invention to active ingredients which have no specific problem of stability.

In the text which follows, the international nonproprietary names have been adopted to designate the active ingredients.

The active ingredient of the freeze-dried pharmaceutical formulations of the present invention may be chosen especially from the group consisting of:

phenylalkanoic acids, for example ketoprofen;
nonsteroid anti-inflammatory agents of the "oxicam" type, for example piroxicam, isoxicam, tenoxicam;
paracetamol;
lysine or arginine acetylsalicylate;
corticosteroids, for example methylprednisolone;

phloroglucinol;

bile acids, for example ursodeoxycholic acid or one of its pharmaceutically acceptable salts with inorganic or organic bases, preferably its sodium salt;

anthracyclines, for example doxorubicin, epirubicin, idarubicin, daunorubicin, pirarubicin;

platinum derivatives, for example cisplatin, oxaliplatin, carboplatin;

derivatives of alkaloids from Vinca minor, for example vinblastine, vincristine;

derivatives of alkaloids from rye ergot, for example dihydroergotamine, dihydroergotoxine, nicergoline;

derivatives of purine or pyrimidine bases, for example acyclovir, gancyclovir, cytarabine;

prostaglandins, for example sulprostone, alprostadil;

benzodiazepines, for example dipotassium clorazepate, devazepide;

beta-lactam antibiotics, for example piperacillin, tazobactam;

macrolide antibiotics, for example erythromycin or one of its derivatives, in general a leukomycin;

antibiotics of the tetracycline family, for example minocycline;

antibiotics of the chloramphenicol type, for example thiamphenicol;

antibiotics of the spiramycin type;

nitrogenous mustards, for example chlorambucin and nitrosoureas, for example carmustine and streptozocin. The nitrogenous mustards and the nitrosoureas are described in greater detail in Pharmacologie by M. Schorderet et al., 1992, 2nd edition, chapter 69, Ed., Frison, Roche, Paris;

$H_2$ antagonists, for example ranitidine, famotidine or one of their pharmaceutically acceptable salts;

omeprazole and its analogues;

vitamins, for example thiamine, riboflavin, nicotinamide, pyridoxine, sodium panthotenate, biotin, ascorbic acid, folic acid, cyanocobalamin, retinol, cholecalciferol, alphatocopherol, cobalamide, hydroxycobalamide;

antitumour agents chosen from taxol, taxotere and their analogues, dacarbazine, methotrexate, plicamycin, thiotepa, streptozocin;

cardiovascular medicines chosen from molsidomine or one of its pharmaceutically acceptable salts, especially its hydrochloride, linsidomine, acetazolamide, meclofenoxate, diltiazem, sodium nitroprussiate;

haematological medicines chosen from ticlopidine or one of its pharmaceutically acceptable salts, especially its hydrochloride, molgramostim, folinic acid;

anticoagulant and antithrombotic medicines chosen from heparin, low-molecular weight heparin in the form of nadroparin calcium, parnaparin sodium, dalteparin sodium, enoxaparin sodium, ardeparin sodium, certoparin sodium, reviparin sodium, minolteparin sodium, natural or synthetic antithrombotic pentasaccharides;

heparinoids, for example lomoparan;

diarginine oxoglutarate and the pharmaceutically acceptable salts of oxoglutaric acid;

plant extracts, for example based on willow, harpagophytum, ginseng, fucus;

a gene, a DNA or RNA fragment intended for gene therapy, an oligonucleotide, an antisense oligonucleotide, nucleotides associated with protein compounds such as for example extracts of ribosome fractions, attenuated or inactivated live viruses;

valproic acid and its analogues;

metopimazine;

moxisylite;

pralidoxime;

deferoxamine;

phenobarbital or other barbiturates;

clomethiazole;

sodium pamidronate, sodium alandronate, sodium risendronate and other diphosphonates active as antiosteoporotic agent, especially {[(4-chlorophenyl)thio] methylene}bis(phosphonate) tiludronate or disodium salt (SR 41319) in hemihydrate or monohydrate form;

$5-HT_2$ antagonists, especially ketanserine, ritanserine, (1Z,2E))-1-(2-fluorophenyl)-3-(4-hydroxyphenyl)-prop-2-en-1-one-O-(2-dimethylaminoethyl)oxime (SR 46349) or one of its pharmaceutically acceptable salts;

antagonists of angiotensin II, especially tasosartan, telmisartan, losartan potassium, losartan combined with hydrochlorothiazide (HCTZ), eprosartan, candesartan cilexetil, valsartan, irbesartan or 2-n-butyl-3-{[2'-(1H-tetrazol-5-yl)biphenyl-4-yl]methyl}-1,3-diazaspiro[4.4]non-1-en-4-one (SR 47436) and its pharmaceutically acceptable salts;

fantofarone or 1-[(p-{3-[(3,4-dimethoxyphenethyl) methylamino]propoxy}phenyl) sulphonyl]-2-isopropylindolizine and its pharmaceutically acceptable salts;

tirapazamine or 3-amino-1,2,4-benzotriazine-1,4-dioxide and its pharmaceutically acceptable salts;

(2S)-1-[(2R,3S)-5-chloro-3-(2-chlorophenyl)-1-(3,4-dimethoxybenzenesulphonyl)-3-hydroxy-2,3-dihydro-1H-indole-2-carbonyl]pyrrolidine-2-carboxamide (SR 49059) and its pharmaceutically acceptable salts;

N,N-dibutyl-3-{4-[(2-butyl-5-methylsulphonamido)-benzofuran-3-ylcarbonyl]phenoxyl}propylamine and its pharmaceutically acceptable salts, especially the hydrochloride (SR 33589);

6-(2-diethylamino-2-methyl)propylamino-3-phenyl-4-propylpyridazine (SR 46559) and its pharmaceutically acceptable salts;

ethyl {(7S)-7-[(2R)-2-(3-chlorophenyl)-2-hydroxy-ethylamino]-5,6,7,8-tetrahydronaphthalen-2-yloxy}-acetate and its pharmaceutically acceptable salts, especially the hydrochloride (SR 58611A);

1-(2,4-dichlorophenyl)-3-(N-piperidin-1-yl-carboxamido)-4-methyl-5-(4-chlorophenyl)-1H-pyrazole and its pharmaceutically acceptable salts, especially the hydrochloride (SR 141716A);

4-{[N-(3,4-dimethoxyphenethyl)]-N-methylamino-propoxyl}-2-benzenesulphonyl-3-isopropyl-1-methylindole (SR 33805) and its pharmaceutically acceptable salts;

2-{[1-(7-chloroquinolin-4-yl)-5-(2,6-dimethoxyphenyl)-1H-pyrazole-3-carbonyl]amino}adamantane-2-carboxylic acid (SR 48692) and its pharmaceutically acceptable salts;

N-cyclohexyl-N-ethyl-3-(3-chloro-4-cyclohexylphenyl) prop-2-enylamine (SR 31747);

(−)-N-methyl-N-[4-(4-acetylamino-4-phenylpiperidino)-2-(3,4-dichlorophenyl)butyl]benzamide (SR 48968) and its pharmaceutically acceptable salts;

(S)-1-{2-[3-(3,4-dichlorophenyl)-1-(3-isopropoxy-phenylacetyl)piperidin-3-yl]ethyl}-4-phenyl-1-azoniabicyclo[2.2.2]octane chloride (SR 140333A) and its pharmaceutically acceptable quaternary salts, for example the benzenesulphonate;

4-amino-1-(6-chloropyrid-2-yl)piperidine and its pharmaceutically acceptable salts, especially the hydrochloride (SR 57227A);

(S)-N-(1-{3-[1-benzoyl-3-(3,4-dichlorophenyl)piperidin-3-yl]propyl}-4-phenylpiperidin-4-yl)N-methylacetamide (SR 142801) and its pharmaceutically acceptable salts;

2-{[4-(2-chlorophenyl) thiazol-2-yl]aminocarbonyl}-indole-1-acetic acid (SR 27897) and its pharmaceutically acceptable salts;

clopidogrel or methyl (+)-(S)-α-(2-chlorophenyl)- 4,5,6,7-tetrahydrothieno-[3,2-c]pyridine-5(4H)-acetate and its pharmaceutically acceptable salts, especially its hydrogen sulphate;

1-(2-naphthalen-2-ylethyl)-4-(3-trifluoromethylphenyl)-1,2,3, 6-tetrahydropyridine hydrochloride (SR 57746A) and its pharmaceutically acceptable salts, especially its hydrochloride;

N,N-dimethyl-N'-(pyridin-3-yl)methyl-N'-[4-(2,4,6-triisopropylphenyl)thiazol-2-yl]ethane-1,2-diamine and its pharmaceutically acceptable salts, especially the fumarate (SR 27417);

2-[(5-(2,6-dimethoxyphenyl)-1-{4-[(3-dimethyl-aminopropyl)methylcarbamoyl]-2-isopropylphenyl}-1H-pyrazole-3-carbonyl)amino]adamantane-2-carboxylic acid and its pharmaceutically acceptable salts (SR 142948A);

3-(1-{2-[4-benzoyl-2-(3,4-difluorophenyl)morpholino-2-yl]ethyl}-4-phenylpiperidin-4-yl)-1,1-dimethylurea and its pharmaceutically acceptable salts (SR 144190A);

3-[N-{4-[4-(aminoiminomethyl)phenyl]-1,3-thiazol-2-yl}-N-(1-carboxymethylpiperidin-4-yl)amino]propionic acid trihydrochloride and its pharmaceutically acceptable salts (SR 121566);

ethyl 3-[N-{4-[4-(amino(N-ethoxycarbonylimino)methyl)phenyl]-1,3-thiazol-2-yl}-N-(1-ethoxycarbonylmethyl)piperidin-4-yl)amino]propionate (SR 121787) and its pharmaceutically acceptable salts;

5-ethoxy-1-[4-(N-tert-butylcarbamoyl)-2-methoxybenzenesulphonyl]-3-spiro-[4-(2-morpholinoethyloxy)cyclohexane]indolin-2-one (SR 121463) and its pharmaceutically acceptable salts.

Most particularly preferred are the formulations of the invention in which the active ingredient is chosen from 2-{[4-(2-enlorophenyl)thiazol-2-yl]aminocarbonyl}-indole-1-acetic acid or its potassium salt, irbesartan, clopidogrel, ursodeoxycholic acid and its sodium salt, 1-(2-naphthalen-2-ylethyl)-4-(3-trifluoromethylphenyl)-1,2,3,6-tetrahydropyridine hydrochloride, N,N-dimethyl-N'-(pyridin- 3-yl)methyl-N'-[4-(2,4,6-triisopropylphenyl)thiazol-2-yl]ethane-1,2-diamine fumarate, 2-[(5-(2,6-dimethoxyphenyl)-1-{4-[(3-dimethylaminopropyl)methylcarbamoyl]-2-isopropylphenyl}-1H-pyrazole-3-carbonyl)amino]adamantane-2-carboxylic acid, 3-(1-{2-[4-benzoyl-2-(3,4-difluorophenyl)morpholino-2-yl]ethyl}-4-phenylpiperidin-4-yl)-1,1-dimethylurea, 3-(N-{4-[4-(aminoiminomethyl)phenyl]-1,3-thiazol-2-yl}-N-(1-carboxymethylpiperidin-4-yl)amino]propionic acid trihydrochloride, ethyl 3-[N-{4-[4-(amino(N-ethoxycarbonylimino)methyl)phenyl]-1,3-thiazol-2-yl}-N-(1-(ethoxycarbonylmethyl)piperidin-4-yl)amino]-propionate, 5-ethoxy-1-[4-(N-tert-butylcarbamoyl)-2-methoxybenzenesulphonyl]-3-spiro-[4-(2-morpholino-ethyloxy)cyclohexane]indolin-2-one and their pharmaceutically acceptable salts.

The following formulations are particularly advantageous:

any formulation obtained by freeze-drying a solution in which the mannitol is at a concentration of 9 mg per ml, the alanine is at a concentration of 18 mg per ml and the active ingredient is 2-{[4-(2-chlorophenyl)thiazol-2-yl] aminocarbonyl}indole-1-acetic acid at a concentration of 1.18 mg per ml or one of its pharmaceutically acceptable salts at an equivalent concentration;

any formulation obtained by freeze-drying a solution in which the mannitol is at a concentration of 10 mg per ml, the alanine is at a concentration of 23 mg per ml and the active ingredient is irbesartan at a concentration of 1 mg per ml or one of its pharmaceutically acceptable salts at an equivalent concentration; and any formulation obtained by freeze-drying a solution in which the mannitol is at a concentration of 9 mg per ml, the alanine is at a concentration of 18 mg per ml and the active ingredient is 1-(2-naphthalen-2-ylethyl)-4-(3-trifluoromethylphenyl)-1,2,3,6-tetrahydropyridine hydrochloride at a concentration of between 0.01 mg and 0.2 mg per ml or one of its pharmaceutically acceptable salts at an equivalent concentration.

A pharmaceutically acceptable salt of any one of the salifiable active ingredients listed above may also be selected as active ingredient.

The pharmaceutical active ingredient is preferably chosen from the group consisting of the potassium salt of the acid SR 27897 designated below as SR 27897B, irbesartan or SR 47436, clopidogrel, ursodeoxycholic acid or its sodium salt, SR 57746A and SR 27417A.

To illustrate the present invention, without however limiting it, evaluations were carried out by choosing, as an example of pharmaceutical active ingredient, SR 27897B, SR 47436 (irbesartan) and SR 57746A. Thus, several solutions containing SR 27897B at 1 mg/ml, a phosphate buffer ($Na_2HPO_4/NaH_2PO_4$) at various molarities and at pH values of between 7.5 and 8.25; mannitol and alanine in a ratio R=mass of mannitol/mass of alanine of between 0.1 and 1 were prepared, freeze-dried and analyzed.

Likewise, several solutions containing SR 47436 at 1 mg/ml, potassium hydroxide in a molar ratio [KOH]/[SR 47436] greater than or equal to 1, alanine alone or a mannitol-alanine mixture in a ratio R=mass of mannitol/mass of alanine of between 0.1 and 1, and ethanol, were prepared, freeze-dried and analyzed.

Finally, a solution containing SR 57746A in hydrochloride form at 0.11 mg/ml, anhydrous citric acid and a mannitol-alanine mixture in a ratio R=mass of mannitol/mass of alanine equal to 0.5 was prepared, freeze-dried and analyzed.

TABLE 1 below indicates the compositions of the solutions studied containing SR 27897B. For each of these formulations, R=0.5 with, as mannitol, alanine and SR 27897B concentration, 9 mg/ml, 18 mg/ml and 1 mg/ml respectively.

TABLE 1

| BATCH NO. | SODIUM PHOSPHATE BUFFER: mM | pH OF THE SODIUM PHOSPHATE BUFFER |
|---|---|---|
| 1 | 5 | 7.5 |
| 2 | 5 | 8 |
| 3 | 10 | 8 |
| 4 | 25 | 8 |
| 5 | 25 | 8.5 |
| 6 | 15 | 8 |
| 7 | 25 | 7.75 |
| 8 | 25 | 8 |
| 9 | 25 | 8.25 |
| 10 | 35 | 8.25 |
| 11 | 25 | 8 |

TABLE 2 below indicates the composition of the freeze-dried solutions studied containing SR 47436.

TABLE 2

| BATCH NO. | mg/ml MANNITOL | mg/ml ALANINE | R | mg/ml KOH | mg/ml SR 47436 |
|---|---|---|---|---|---|
| 12 | 10 | 18 | 0.55 | 0.137 | 1 |
| 13 | 10 | 23 | 0.43 | 0.137 | 1 |

TABLE 3 below indicates the composition of the freeze-dried solutions studied containing SR 57746A in hydrochloride form.

TABLE 3

| BATCH NO. | mg/ml MANNITOL | mg/ml ALANINE | R | mg/ml ANHYDROUS CITRIC ACID | mg/ml SR 57746A | mg/m/ POLYSORBATE 80 |
|---|---|---|---|---|---|---|
| 14 | 9 | 18 | 0.5 | 7.7 | 0.11 | 0 |
| 15 | 9 | 18 | 0.5 | 7.7 | 0.11 | 1 |

The turbidity of the freeze-dried products taken up in solution will be determined with the aid of a Ratio Hach 18900-00 turbidimeter. The results will be expressed in nephelometric turbidity units (NTU) defined by Standard methods for the examination of water and waste-water of the American Public Health Association.

The organoleptic criteria for the freeze-dried products will be examined visually and will take into account the colour of the freeze-dried product, its structure (collapsed or otherwise), as well as the observation of a possible phase shift between the crust and the crumb of the freeze-dried product.

The water content of the freeze-dried products will be determined by coulometry according to the method described in Ph. Fr. Xth Ed. V. 3.5.6. A., by injecting 2 ml of methanol into the vial of freeze-dried product with the aid of a syringe. The water content will be expressed in percentage by weight of the freeze-dried product.

X-ray diffractometric analysis on the freeze-dried products will be carried out on a SIEMENS D500 TT diffractometer; source: CuKal; generator: 40 KV, 25 mA; back monochromator; slits: 1/1/0.16/0.6; sampling on a pyrex support; scanning range: 40 to 400 per minute for Bragg 2 theta.

Differential scanning calorimetry (DSC) will be carried out using the Perkin Elmer DSC 7 apparatus with the following characteristics: calibration with indium and lead, sampling between 5 and 10 mg in a 50 µl capsule, initial temperature of 10° C., heating rate of 10° C./minute, final temperature 300° C.

The SR 27897B assay will be carried out by liquid chromatography (Ph. Eur. 2 (1) V. 6.20.4. ) at 254 nm using a C18 graft column 25 cm long, 4.6 mm internal diameter and particle size 10 µm (Bischoff reference 25461840). The mobile phase will consist of a volume for volume mixture of acetate buffer pH 4.0 (glacial acetic acid and concentrated ammonium hydroxide Merck) and of acetonitrile for chromatography (Sharlau reference Ac33). The control solution will consist of a solution of SR 27897B (provided by Sanofi Recherche) at 50 µg per ml of methanol (Merck reference 6009). The solution to be analyzed will be obtained by dissolving the freeze-dried product in 100 ml of ultrapurified water (Millipore, "Milli-Q" water). The flow rate will be 2 ml/min. The specific peak surface area obtained after injection of 20 µl of control solution and then of solution to be analyzed will be calculated for each of the chromatograms. The SR 27897B content of the freeze-dried product, expressed in mg/vial, will be determined from the calculation of these two surface areas.

The assay of the related substances (impurities) of SR 27897B in the freeze-dried product during preservation, a parameter indicative of the stability of the product, will also be carried out by liquid chromatography on a C18 graft column (Bischoff reference 25461840). The mobile phase will consist of a gradient of acetonitrile and acetate buffer pH 4.0 whose composition is indicated in TABLE A:

TABLE A

| TIME (minute) | ACETONITRILE (volume) | ACETATE BUFFER pH 4.0 (volume) |
|---|---|---|
| 0 | 20 | 80 |
| 5 | 30 | 70 |
| 15 | 60 | 40 |
| 25 | 70 | 30 |
| 28 | 20 | 80 |
| 40 | 20 | 80 |

The control solution will consist of a solution of SR 27897B (Sanofi Recherche) at 10 µg per ml of methanol. The solution to be analyzed will be obtained by dissolving the contents of a freeze-dried vial in 5 ml of methanol. The flow rate will be 2 ml/min. The specific peak surface area of the unknown impurities obtained on the chromatograms after injection of 20 µl of the solution to be analyzed, expressed in terms of the specific peak surface area of SR 27897B obtained after injection of 20 µl of the control solution, will be calculated in the same manner. The content of each of the unknown impurities and the overall content of impurities of the freeze-dried SR 27897B, expressed in percentage by weight of the product, can be determined from these calculations.

The SR 47436 assay will be carried out by HPLC liquid chromatography (Ph. Eur. 2 (1) V 6.20.4.) at 220 nm using a C18 graft silica column made of stainless steel, 25 cm long, 8 mm external diameter and 4 mm internal diameter, spherical silica of diameter 7 μm and of 120 Å pore diameter having undergone an "end capping" treatment (reference column 720042 supplied by Chromoptic). The mobile phase will consist of a mixture of 60 volumes of phosphate buffer solution pH 3.0 (phosphoric acid Prolabo reference 20624295, triethylamine Fluka reference 90340) and of 40 volumes of acetonitrile for chromatography (Merck reference 14291) with a flow rate of 1 ml/min.

The first control solution will consist of a solution of SR 47436 (Sanofi Recherche) at 0.5 mg per ml of mobile phase. The second control solution will consist of a solution containing 0.5 mg of SR 47436 and 0.5 mg of impurity corresponding to the opening product (Sanofi Recherche) per ml of mobile phase. The solution to be analyzed will be obtained by dissolving the freeze-dried product in 10 ml of mobile phase. It will be checked by successive injection of the first and second control solutions that the operating conditions are satisfactory (resolution factor greater than 2 between the two peaks for an injection of 10 μl of the second control solution, coefficient of variation of the surface area of the peak less than or equal to 1% for a series of 5 injections of 10 μl of the first control solution). After injection of 10 μl of each control solution and of 20 μl of each solution to be analyzed, the SR 47436 content in mg per freeze-dried product will be determined by calculating the specific peak surface areas obtained on the chromatograms.

The assay of the related substances (impurities) of SR 47436 will be carried out by HPLC liquid chromatography (Ph. Eur. 2 (1) V 6.20.4.) at 220 nm using a C18 graft silica column (cf. assay of SR 47436). The mobile phase will consist of a mixture of 60 volumes of phosphate buffer pH 3.1 and 40 volumes of acetonitrile for chromatography with a flow rate of 1 ml/min. The two control solutions will consist, for the first, of a solution of SR 47436 (Sanofi Recherche) at 0.5 mg per ml of methanol (supplied by SDS under the reference 0930221) and for the second, of a solution of SR 47436 at 0.5 μg per ml of methanol. The solution to be analyzed will be obtained by dissolving the freeze-dried product in 10 ml of water for injectable preparations (IP). The analysis should be carried out within half an hour at the latest after the reconstitution. The existence of satisfactory operating conditions will be checked by successive injections of 10 μl of water for injectable preparations and 10 μl of the two control solutions (retention time of the principle peak similar for the two controls, signal to noise ratio greater than or equal to 10 for the first control). After injecting 10 μl of the solution to be analyzed, the content per related substance and the overall content of related substances (impurities) expressed in percentage of product weight will be determined by calculating the specific peak surface areas obtained on the chromatograms.

The SR 57746A assay (Sanofi Recherche) will be carried out by liquid chromatography at 224 nm using a C18 graft silica column 25 cm long, 4 mm internal diameter and particle size 7 μm (Macherey Nagel, reference 720042). The mobile phase will consist of a mixture of 45 volumes of acetonitrile for chromatography (Rathburn reference RH 1016) and 55 volumes of buffer solution pH 3.0 (prepared by diluting 5.5 ml of phosphoric acid in 950 ml of filtered demineralized water (Millipore Alpha-Q), then by adjusting the pH to 3.0 with a triethylamine solution (Fluka, reference 90340) then by adding 10 ml of acetonitrile and by filling to 1000 ml with filtered demineralized water). The control solution will consist of an SR 57746A solution at 15.0 mg per 100 ml of methanol (Carlo Erba, reference 414814). The solution to be analyzed will be obtained by dissolving the freeze-dried product in 3.0 ml of a mixture consisting of 25 volumes of methanol and 75 volumes of filtered demineralized water. The flow rate will be 1 ml per minute. The specific peak surface area obtained after injection of 10 μl of control solution and then of solution to be analyzed will be measured for each of the chromatograms. The SR 57746A content of the freeze-dried product, expressed in mg/vial, can be determined from the measurement of the two surface areas.

The assay of the related substances (impurities) of SR 57746A in the freeze-dried product during preservation will be also carried out by liquid column chromatography with the chromatographic conditions described in "Assays" in (Ph. Eur. 2 (1) V.6.20.4.). The control solution will consist of a solution of SR 57746A at 0.15 μg per ml of methanol. The solution to be analyzed will be obtained by dissolving the contents of the freeze-dried product in 3 ml of a mixture of 25 volumes of methanol and of 75 volumes of filtered demineralized water. The flow rate will be 1 ml per minute. The specific peak surface area of the unknown impurities obtained on the chromatograms after injection of 10 μl of the solution to be analyzed, expressed in terms of the specific peak surface area of SR 57746A obtained after injection of 10 μl of control solution will be measured in the same way. The content of each of the unknown impurities and the overall content of impurities of the freeze-dried SR 57746A, expressed as percentage in terms of surface area, can be determined from these measurements.

The analytical results obtained using these various methods are described below.

TABLE 4 below represents the results of the initial controls carried out on the freeze-dried products of SR 27897B for the water content (in % by weight of the freeze-dried product), the glass transition temperature Tg (in ° C.) determined by DSC, and on the freeze-dried products taken up in water for IP for the turbidity (in NTU) and the pH.

TABLE 4

| Batch No. | % Water | Tg ° C. | Turbidity NTU | pH |
| --- | --- | --- | --- | --- |
| 1 | 0.39 | 27 | 58 | 7.25 |
| 2 | 0.47 | 25 | 23 | 7.2 |
| 3 | 0.6 | 27 | 11 | 7.4 |
| 4 | 0.91 | 35 | 2.2 | 7.6 |
| 5 | 0.89 | 40 | 29 | 7.5 |
| 6 | 0.61 | 36.7 | 17 | 7.6 |
| 7 | 0.93 | 45.5 | 33 | 7.6 |
| 8 | 1.07 | 46.1 | 1.4 | 7.8 |
| 9 | 1.04 | 45.7 | 0.5 | 7.7 |
| 10 | 1.94 | 45.8 | 0.8 | 7.8 |
| 11 | | | 4.5 | 7.6 |

By way of an additional example, several batches of freeze-dried product of SR 27897B were monitored for stability at 50° C., 25° C., 40° C. and 50° C. for 1 month, 3 months and 6 months.

TABLE 5 which represents the total content of related substances (impurities), expressed in % by weight of initial SR 27897B, found in the freeze-dried products of SR 27897B after 1 month of storage shows that the stability is excellent after this period of storage.

TABLE 5

| Batch No. | % Impurities at 5° C. | % Impurities at 25° C. | % Impurities at 40° C. | % Impurities at 50° C. |
|---|---|---|---|---|
| 1 | <0.27 | <0.26 | | <0.25 |
| 2 | <0.23 | <0.26 | | <0.24 |
| 3 | <0.23 | <0.26 | | <0.25 |
| 4 | <0.26 | <0.24 | | <0.24 |
| 5 | <0.23 | <0.25 | | <0.26 |
| 6 | | | <0.1 | |
| 7 | | | <0.1 | |
| 8 | | | <0.1 | |
| 9 | | | <0.1 | |
| 10 | | | <0.1 | |
| 11 | | <0.1 | <0.1 | |

TABLE 6 which represents the total content of related substances (impurities) found in the freeze-dried products of SR 27897B after 3 months of storage at 50° C., shows that the stability is excellent after this period of storage.

TABLE 6

| Batch No. | % Impurities at 50° C. |
|---|---|
| 1 | <0.1 |
| 2 | <0.1 |
| 3 | <0.1 |
| 4 | <0.1 |
| 5 | <0.1 |

Finally, TABLE 7 represents the total content of related substances (impurities) found in the freeze-dried products of SR 27897B after 6 months of storage at 5° C. and 40° C., shows that the stability is also excellent after this period of storage.

TABLE 7

| Batch No. | % Impurities at 5° C. | % Impurities at 40° C. |
|---|---|---|
| 7 | <0.1 | 0.13 |
| 8 | <0.1 | 0.1 |
| 9 | <0.1 | 0.1 |
| 11 | | <0.1 |

X-ray diffraction.

The result of the X-ray diffraction analysis on the powder of two freeze-dried products containing a mannitol/alanine mixture in a ratio R=mass of mannitol/mass of alanine=0.5 is indicated in FIG. 1, diffractograms 1 and 2. The diffractograms 3 and 4 of FIG. 1 represent the controls alanine and mannitol. As can be observed in this figure, the line situated between 10° and 11°, characteristic of crystallized mannitol, is not obtained for the two freeze-dried products of SR 27897B. Thus, for R=0.5, the alanine alone is in crystallized form, the mannitol being, for its part, in amorphous form.

Differential scanning calorimetry.

Figure 2:
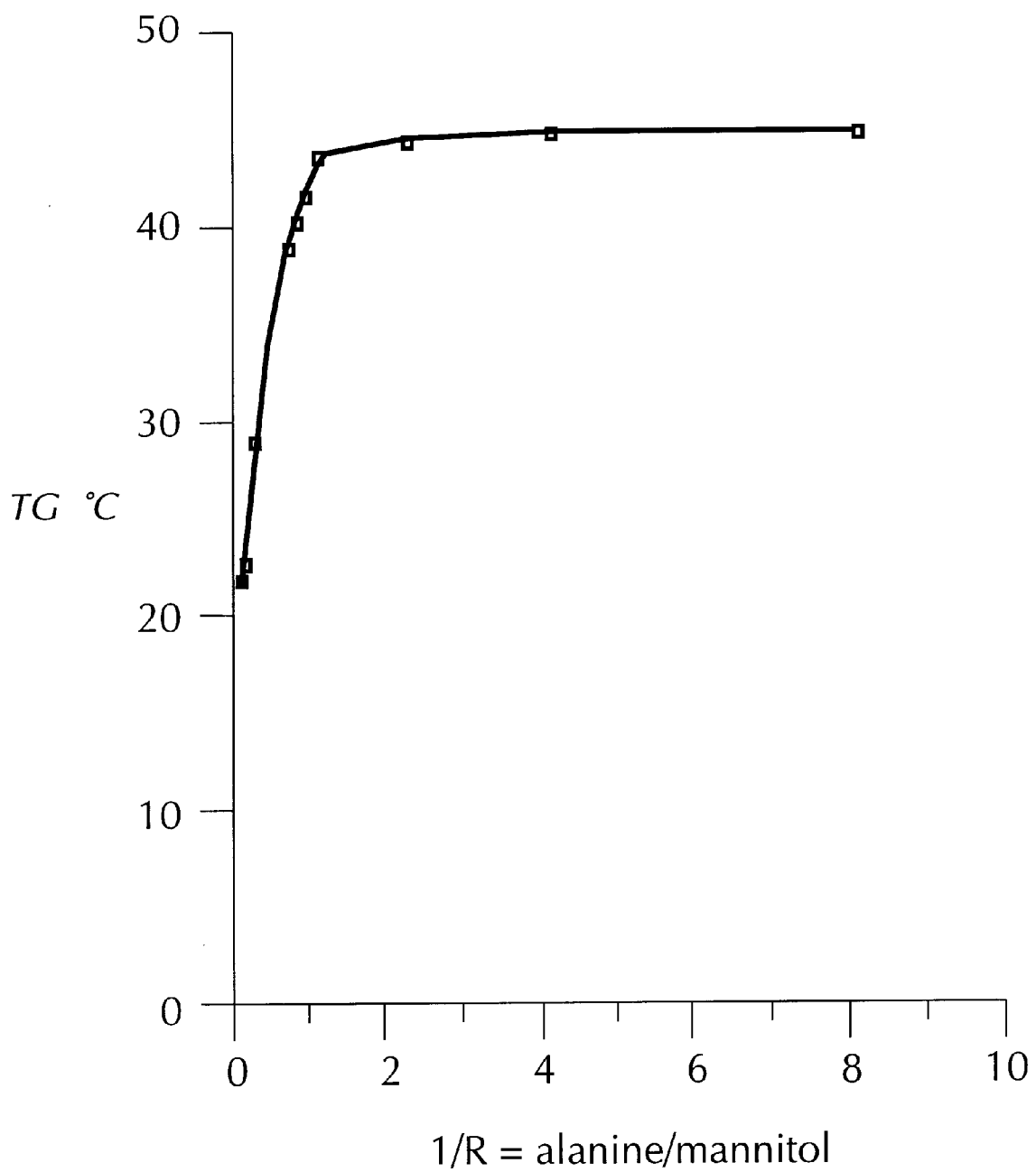

FIG. 2 represents the influence of the alanine to mannitol mass ratio on the glass transition temperature of the freeze-dried products. This figure shows us that the maximum glass transition temperature is obtained for (1/R)>1, that is to say for R of between 0 and 1. In general, the glass transition temperature is representative of the maximum temperature for stability of the freeze-dried product. Thus, the maximum temperature for stability of the freeze-dried product is reached for R of between 0 and 1.

TABLE 8 below represents the results of the initial controls carried out on the freeze-dried products of SR 47436 for the water content, the total content of related substances (impurities) and on the freeze-dried products taken up in water for IP, for the pH.

TABLE 8

| Batch No. | % Water | % Impurities | pH |
|---|---|---|---|
| 12 | 0.5% | 0.24 | 6.6 |
| 13 | 0.2 | 0.1 | 6.7 |

TABLE 9 below represents the total content of related substances expressed as percentage purity in terms of SR 47436 of the freeze-dried products of SR 47436 batch 12 after 1 week and 2 weeks of storage at 5° C., 25° C., 35° C. and 50° C.

TABLE 9

| Batch No. 12 | 5° C. | 25° C. | 35° C. | 50° C. |
|---|---|---|---|---|
| 1 week | 99.89 | 99.89 | 99.71 | 98.47 |
| 2 weeks | 99.90 | 99.82 | 99.47 | 97.05 |

TABLE 10 below represents the total contents of related substances expressed as percentage of impurities, of the freeze-dried products of SR 47436 batch 13 after 3 months, 6 months and 9 months of storage at 5° C., 25° C. and 35° C.

TABLE 10

| Batch No. 13 | 5° C. | 25° C. | 35° C. |
|---|---|---|---|
| 3 months | 0.1% | 0.2% | 0.3% |
| 6 months | 0.2% | 0.3% | 0.6% |
| 9 months | 0.3% | 0.3% | — |

TABLE 11 below represents the total contents of related substances expressed as percentage of impurities, of the freeze-dried products of SR 57746A after 1 month and 3 months of storage at 5° C., 25° C. and 40° C. and of a freeze-dried product of SR 57746A reconstituted immediately (reference).

TABLE 11

| Batches N° 14 and 15 | 5° C. | 25° C. | 40° C. |
|---|---|---|---|
| Reference | | <0.1% | |
| 1 month | <0.1% | <0.1% | <0.1% |
| 3 months | <0.1% | <0.1% | <0.1% |

EXAMPLE 1

Composition of a freeze-dried product of SR 27897 (base) to be taken up in 1 ml of water for IP.

| CONSTITUENTS | Unit formula in (mg) |
|---|---|
| SR 27897B* | 1.18 mg |
| Apyrogenic alanine | 18.0 mg |
| Mannitol | 9.0 mg |
| Apyrogenic monosodium phosphate dihydrate | 0.3 mg |

| CONSTITUENTS | Unit formula in (mg) |
|---|---|
| Apyrogenic disodium phosphate dodecahydrate | 8.5 mg |
| White glass vial type 1 of 3 ml | 1 |
| Grey chlorobutyl pillar stopper | 1 |
| Blue flip-off aluminium capsule diameter 13 mm | 1 |

*corresponding to 1 mg of SR 27897 acid

EXAMPLE 2

Composition of a freeze-dried product of SR 27897 (base) to be taken up in 5 ml of water for IP.

| CONSTITUENTS | Unit formula in (mg) |
|---|---|
| SR 27897B* | 5.9 mg |
| Apyrogenic alanine | 90.0 mg |
| Apyrogenic mannitol | 45.0 mg |
| Apyrogenic monosodium phosphate dihydrate | 1.5 mg |
| Apyrogenic disodium phosphate dodecahydrate | 42.5 mg |
| White glass vial type 1 of 20 ml | 1 |
| Grey chlorobutyl pillar stopper diameter 20 mm | 1 |
| Blue flip-off aluminium capuule diameter 20 mm | 1 |

*corresponding to 5 mg of SR 27897 acid

EXAMPLE 3

Composition of a freeze-dried product of SR 47436 at 5 mg to be taken up in 5 ml of water for IP.

| CONSTITUENTS | Unit formula in (mg) |
|---|---|
| SR 47436 | 5.0 mg |
| Apyrogenic alanine | 115.0 mg |
| Apyrogenic mannitol | 50.0 mg |
| Potassium hydroxide | 0.687 mg |
| White glass vial type 1 of 20 ml | 1 |
| Grey chlorobutyl pillar stopper diameter 20 mm | 1 |
| Aluminium capsule with operculum, diameter 20 mm | 1 |

EXAMPLE 4

Composition of a freeze-dried product of SR 57746A (hydrochloride) to be taken up in 4 ml of water for IP.

| CONSTITUENTS | Unit formula in (mg) |
|---|---|
| SR 57746A | 0.44 mg |
| Apyrogenic alanine | 72.0 mg |
| Apyrogenic mannitol | 36.0 mg |
| Apyrogenic anhydrous citric acid | 30.8 mg |
| White glass vial type 1 of 20 ml | 1 |
| Grey chlorobutyl pillar stopper diameter 20 mm | 1 |
| Blue flip-off aluminium capsule diameter 20 mm | 1 |

EXAMPLE 5

Composition of a solution of SR 57746A (hydrochloride) to be freeze-dried, expressed in concentration for final volumes of solution which may be as high as 100 ml by addition of a sufficient quantity of water for IP.

| CONSTITUENTS | Unit formula expressed in mg/ml |
|---|---|
| SR 57746A | 0.11 mg/ml |
| Apyrogenic alanine | 18.0 mg/ml |
| Apyrogenic mannitol | 9.0 mg/ml |
| apyrogenic anhydrous citric acid | 7.7 mg/ml |
| Water for injectable preparations | qs 1 ml |
| White glass vial type 1 | 1 |
| Grey chlorobutyl pillar stopper | 1 |
| Blue flip-off aluminium capsule | 1 |

EXAMPLE 6

Composition of a freeze-dried product of SR 57746A (hydrochloride) containing from 0.01 mg to 0.2 mg of SR 57746A (hydrochloride) to be taken up in 1 ml of water for IP.

| CONSTITUENTS | Unit formula in (mg) |
|---|---|
| Apyrogenic alanine | 18.0 mg |
| Apyrogenic mannitol | 9.0 mg |
| Apyrogenic anhydrous citric acid | 7.7 mg |
| White glass vial type 1 of 3 ml | 1 |
| Grey chlorobutyl pillar stopper | 1 |
| Blue flip-off aluminium capsule diameter 13 mm | 1 |

EXAMPLE 7

Composition of a freeze-dried product of SR 57746A (hydrochloride) to be taken up in 4 ml of water for IP.

| CONSTITUENTS | Unit formula in (mg) |
|---|---|
| SR 57746A | 0.44 mg |
| Apyrogenic alanine | 72.0 mg |
| Apyrogenic mannitol | 36.0 mg |
| Apyrogenic anhydrous citric acid | 30.8 mg |
| Polysorbate 80 | 4.0 mg |
| White glass vial type 1 of 20 ml | 1 |
| Grey chlorobutyl pillar stopper diameter 20 mm | 1 |
| Blue flip-off aluminium capsule diameter 20 mm | 1 |

EXAMPLE 8

Composition of a solution of SR 57746A (hydrochloride) to be freeze-dried, expressed in concentration for final volumes of solution which may be as high as 100 ml by addition of a sufficient quantity of water for IP.

| CONSTITUENTS | Unit formula expressed in mg/ml |
|---|---|
| SR 57746A | 0.11 mg/ml |
| Apyrogenic alanine | 18.0 mg/ml |
| Apyrogenic mannitol | 9.0 mg/ml |
| apyrogenic anhydrous citric acid | 7.7 mg/ml |
| Polysorbate 80 | 1.0 mg/ml |
| Water for injectable preparations | qs 1 ml |
| White glass vial type 1 | 1 |
| Grey chlorobutyl pillar stopper | 1 |
| Blue flip-off aluminium capsule | 1 |

EXAMPLE 9

Composition of a freeze-dried product of SR 57746A (hydrochloride) containing from 0.01 mg to 0.2 mg of SR 57746A (hydrochloride) to be taken up in 1 ml of water for IP.

| CONSTITUENTS | Unit formula in (mg) |
|---|---|
| Apyrogenic alanine | 18.0 mg |
| Apyrogenic mannitol | 9.0 mg |
| Apyrogenic anhydrous citric acid | 7.7 mg |
| Polysorbate 80 | 1.0 mg |
| White glass vial type 1 of 3 ml | 1 |
| Grey chlorobutyl pillar stopper | 1 |
| Blue flip-off aluminium capsule diameter 13 mm | 1 |

What is claimed is:

1. Freeze-dried formulation consisting of an amorphous phase and a crystalline phase, which is pharmaceuticlly acceptable, comprising at least one nonprotein active ingredient, characterized in that it contains mannitol and alanine in a ratio R of between 0.1 and 1, R representing the mass of mannitol to the mass of alanine, it being understood that formulations further comprising one or more matrix forming agent selected from the group consisting of pectins, gelatins, soy fiber proteins and mixtures thereof are excluded.

2. Formulation according to claim 1, in which the active ingredient is combined with another active ingredient of a protein nature.

3. Formulation according to claim 1 or 2, comprising, in addition, at least one additional compound selected from the group consisting of a buffer, a surfactant, a preservative, a salt, an antioxidant and a chelating agent.

4. Formulation according to claim 1 or 2, for the reconstitution of a solution for its administration via the parenteral route.

5. Formulation according to claim 1 or 2, for the reconstitution of a solution for its administration via the oral route.

6. Formulation according to claim 4, for the reconstitution of an injectable solution.

7. Formulation according to claim 1, which is directly administrable via the oral route.

8. Formulation according to claim 1, in which the active ingredient is chosen from 2-{[4-(2-chlorophenyl)thiazol-2-yl]aminocarbonyl}indole-1-acetic acid or its potassium salt, irbesartan, clopidogrel, ursodeoxycholic acid and its sodium salt, 1-(2-naphthalen-2-ylethyl)-4-(3-trifluoromethylphenyl)-1,2,3,6-tetrahydropyridine hydrochloride, N,N-dimethyl-N'-(pyridin-3-yl)methyl-N'-[4-(2,4,6-triisopropylphenyl)thiazol-2-yl]ethane-1,2-diamine fumarate, 2-[(5-(2,6-dimethoxyphenyl)-1-{4-[(3-dimethylaminopropyl)methylcarbamoyl]-2-isopropylphenyl}-1H-pyrazole-3-carbonyl)amino] adamantane-2-carboxylic acid, 3-(1-{2-[4-benzoyl-2-(3,4-difluorophenyl)morpholino-2-yl]ethyl}-4-phenylpiperidin-4-yl)-1,1-dimethylurea, 3-[N-{4-[4-(aminoiminomethyl) phenyl]-1,3-thiazol-2-yl}-N-(1-carboxymethylpiperidin-4-yl)-amino]propionic acid trihydrochloride, ethyl 3-[N-{4-[4-(amino (N-ethoxycarbonylimino) methyl)phenyl]-1,3-thiazol-2-yl}-N-(1-(ethoxycarbonylmethyl)piperidin-4-yl) amino]propionate, 5-ethoxy-1-[4-(N-tert-butyl-carbamoyl)-2-methoxybenzenesulphonyl]-3-spiro-[4-(2-morpholinoethyloxy)cyclohexane]indolin-2-one and their pharmaceutically acceptable salts.

9. Formulation according to claim 1, obtained after freeze-drying a solution in which the mannitol is at a concentration of 9 mg per ml, the alanine is at a concentration of 18 mg per ml and the active ingredient is 2-{[4-(2-chlorophenyl)thiazol-2-yl]aminocarbonyl}-indole-1-acetic acid at a concentration of 1.18 mg per ml or one of its pharmaceutically acceptable salts at an equivalent concentration.

10. Formulation according to claim 1, obtained after freeze-drying a solution in which the mannitol is at a concentration of 10 mg per ml, the alanine is at a concentration of 23 mg per ml and the active ingredient is irbesartan at a concentration of 1 mg per ml or one of its pharmaceutically acceptable salts at an equivalent concentration.

11. Formulation according to claim 1, obtained after freeze-drying a solution in which the mannitol is at a concentration of 9 mg per ml, the alanine is at a concentration of 18 mg per ml and the active ingredient is 1-(2-naphthalen-2-ylethyl)-4-(3-trifluoromethylphenyl)-1,2,3,6-tetrahydropyridine hydrochloride at a concentration of between 0.01 mg and 0.2 mg per ml or one of its pharmaceutically acceptable salts at an equivalent concentration.

12. Process for the stabilization of a nonprotein active ingredient contained in a freeze-dried pharmaceutically acceptable formulation, wherein the freeze-dried formulation is obtained starting from an aqueous solution comprising said active ingredient, mannitol and alanine in a ratio R of between 0.1 and 1, R representing the mass of mannitol to the mass of alanine.

13. Formulation according to claim 1, in which the active ingredient is selected from the group consisting of phenylalkanoic acids, oxicam nonsteroid anti-inflammatory agents, paracetamol, lysine or arginine acetylsalicylate, bile acids, corticosteroids, anthracyclines, phloroglucinol, platinum derivatives, derivatives of alkaloids from Vinca minor, derivatives of alkaloids from rye ergot, derivatives of purine or pyrimidine bases, prostaglandins, benzodiazepines, antibiotics, nitrosoureas, nitrogenous mustards, $H_2$ antagonists, omeprazole, vitamins, antitumour agents, cardiovascular medcines, haematological medicines, anticoagulant and antithrombotic medicine, heparinoids, diarginine oxoglutarate, plant extracts, nucleotides, valproic acid and its analogues, metopimazine, moxisylite, active bisphosphonates as antiosteoporotic agent, pralidoxime, deferoxamine, barbiturates, clomethiazole, 5-$HT_2$ antagonists, antagonists of angiotensin II, fantofarone, tirapazamine, (2S)-1-[(2R,3S)-5-chloro-3-(2-chlorophenyl)-1-(3,4-dimethoxybenzenesulphonyl)-3-hydroxy-2,3-dihydro-1H-indole-2-carbonyl]pyrrolidine-2-carboxamide, N,N-dibutyl-3-{4-[(2-butyl-5-methylsulphonamido) benzofuran-3-ylcarbonyl]phenoxyl}propylamine, 6-(2- diethylamino-2-methyl)propylamino-3-phenyl-4-propylpyridazine, ethyl {(7S)-7-[(2R)-2-(e-chlorophenyl)-2-hydroxyethylamino]-5,6,7,8-tetrahydronaphthalen-2-yloxy}acetate, 1-(2,4-dichlorophenyl)-3-(N-piperidin-1-ylcarboxamido)4-methyl-5-(4-chlorophenyl)-1H-pyrazole, 4-{[N-(3,4-dimethoxyphenethyl)]-N-methylaminopropoxyl}-2-benzenesulphonyl-3-isopropyl-1-methylindole, 2-{[1-(7-chloroquinolin-4-yl)-5-(2,6-dimethoxy-phenyl)-1H-pyrazole-3-carbonyl]amino}adamantane-2-carboxylic acid, (N-cyclohexyl-N-ethyl-3-(3-chloro-4-cyclohexylphenyl)prop-2-enylamine, (−)-N-methyl-N-[4-(4-acetylamino-4-phenylpiperidino)-2-(3,4-dichlorophenyl)butyl]benzamide, (S)-1-{2-[3-(3,4-dichlorophenyl)-1-(3-isopropoxyphenylacetyl)piperidin-3-yl]ethyl}-4-phenyl-1-azoniabicyclo[2.2.2]octane chloride and its pharmaceutically acceptable quaternary salts, 4-amino-1-(6-chloropyrid-2-yl)piperidine, (S)-N-(1-{3-[1-benzoyl-3-(3,4-dichlorophenyl)piperidin-3-yl]propyl}4-phenylpiperidin4-yl)-N-methylacetamide, 2-{[4-(2-chlorophenyl)thiazol-2-yl]aminocarbonyl}indole-1-acetic acid, clopidogrel, 1-(2-naphthalen-2-ylethyl)4-(3-trifluoromethylphenyl)-1,2,3,6-tetrahydropyridine hydrochloride, N,N-dimethyl-N'-(pyridin-3-yl)methyl-N'-[4-(2,4,6-triisopropylphenyl)-thiazol-2-yl]ethane-1,2-diamine, and their pharmaceutically acceptable salts.

\* \* \* \* \*